United States Patent [19]
Sudol et al.

[11] Patent Number: 5,622,175
[45] Date of Patent: Apr. 22, 1997

[54] MINIATURIZATION OF A ROTATABLE SENSOR

[75] Inventors: Wojtek Sudol, Burlington; Francis E. Gurrie, Ipswich, both of Mass.

[73] Assignee: Hewlett-Packard Company, Palo Alto, Calif.

[21] Appl. No.: 536,034

[22] Filed: Sep. 29, 1995

[51] Int. Cl.[6] .................................................. A61B 8/00
[52] U.S. Cl. ............................................................ 128/662.03
[58] Field of Search ............................ 128/660.1, 662.03, 128/662.06; 310/334–336; 29/25.35

[56] References Cited

U.S. PATENT DOCUMENTS

| | | | |
|---|---|---|---|
| 5,320,104 | 6/1994 | Fearnside et al. | 128/662.06 X |
| 5,351,691 | 10/1994 | Brommersma | 128/662.06 |
| 5,353,798 | 10/1994 | Sieben | 128/662.06 |
| 5,402,793 | 4/1995 | Gruner et al. | 128/662.06 |

*Primary Examiner*—Francis Jaworski
*Attorney, Agent, or Firm*—Pamela L. Kee

[57] ABSTRACT

A miniature rotatable sensor include an acoustic face positioned over a layer of attenuating material. Between the acoustic face and the attentuating material is a flexible circuit that contacts the acoustic face and has circuit edge that extend beyond the attenuating material to create an inner portion. The inner portion further includes a radial slot extending throught the perimeter of the attenuating material. The circuit edges are folded into the radial slot such that the flexible circuit exits tangential to the diameter of the sensor.

4 Claims, 5 Drawing Sheets

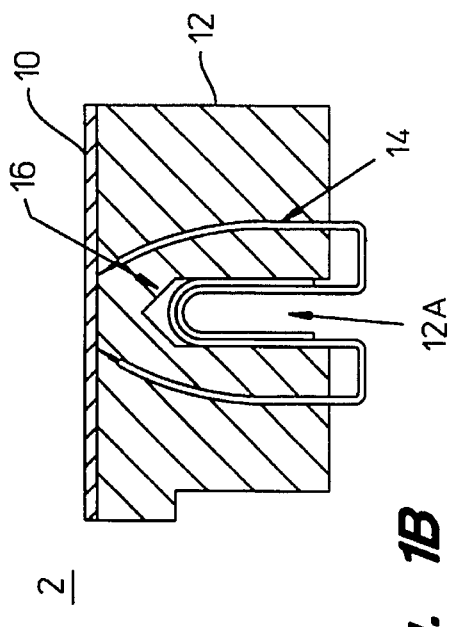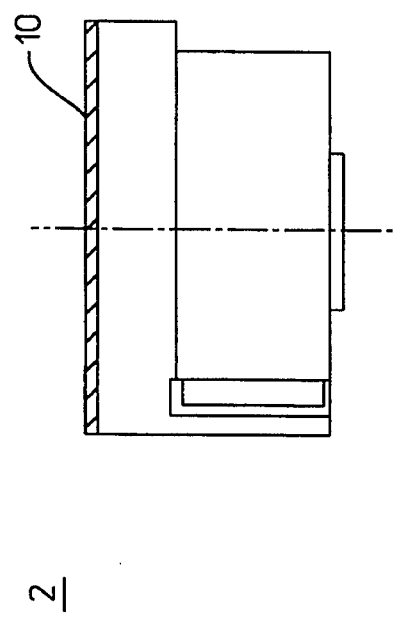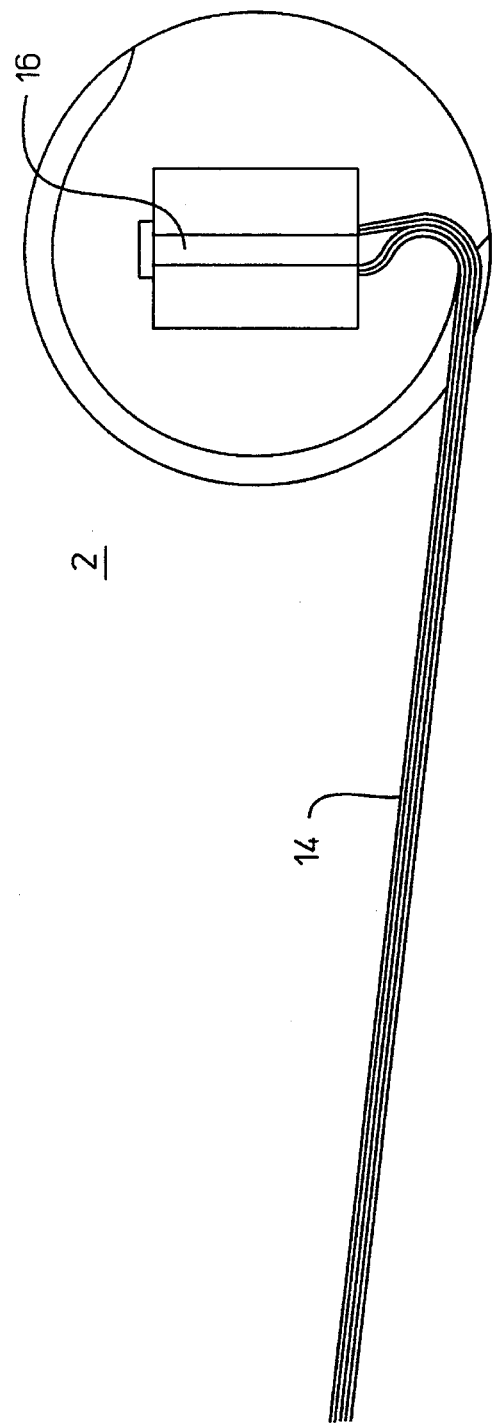
Fig. 1A
Fig. 1B
Fig. 1C

MINIATURIZATION OF A ROTATABLE SENSOR

FIELD OF THE INVENTION

This invention is directed toward medical imaging using ultrasound transducers and more specifically towards reducing the size of the transducers used in transesophageal imaging.

BACKGROUND OF THE INVENTION

Echo ultrasound is an established technique in the area of medical imaging. Typically, an ultrasound imaging system has electronics for remote excitation of an ultrasound transducer array or probe to obtain cross-sectional images of the internal organs. In transesophageal imaging, an ultrasound probe is inserted into a patient's esophagus. Multi plane transesophageal imaging allows a diagnostician to view an image of a desired cross-section of the patient's heart. To obtain multiple cross-sectional images, the transducer array rotates within the tip of the probe. The size of the probe is limited by the physical connection from the rotatable transducer array to the electrical circuit. The existing multi plane transesophageal probe head size is typically 19 mm in diameter which may cause discomfort for patients having a small esophagus.

A probe having a reduced size of the probe head is desirable to minimize the patient's discomfort during an ultrasound procedure. A smaller probe would allow patients with small esophagus, such as children, the same level of diagnostic care as those with larger esophagus.

SUMMARY OF THE INVENTION

A miniature rotatable sensor includes an acoustic face positioned over a layer of attenuating material. The flexible circuit that contacts the acoustic face extends beyond the attenuating material to create an inner portion and the dynamic region. The back side of the attenuating material includes an metal portion with an central cavity in the shape of a radial slot. The inner portions of the flex further are folded into the radial slot such that the flexible circuit exits tangentially to the diameter of the sensor.

BRIEF DESCRIPTION OF THE DRAWINGS

FIGS. 1A–C illustrate a preferred embodiment for a miniature rotatable sensor.

DETAILED DESCRIPTION OF THE PREFERRED EMBODIMENTS

Figure 2:
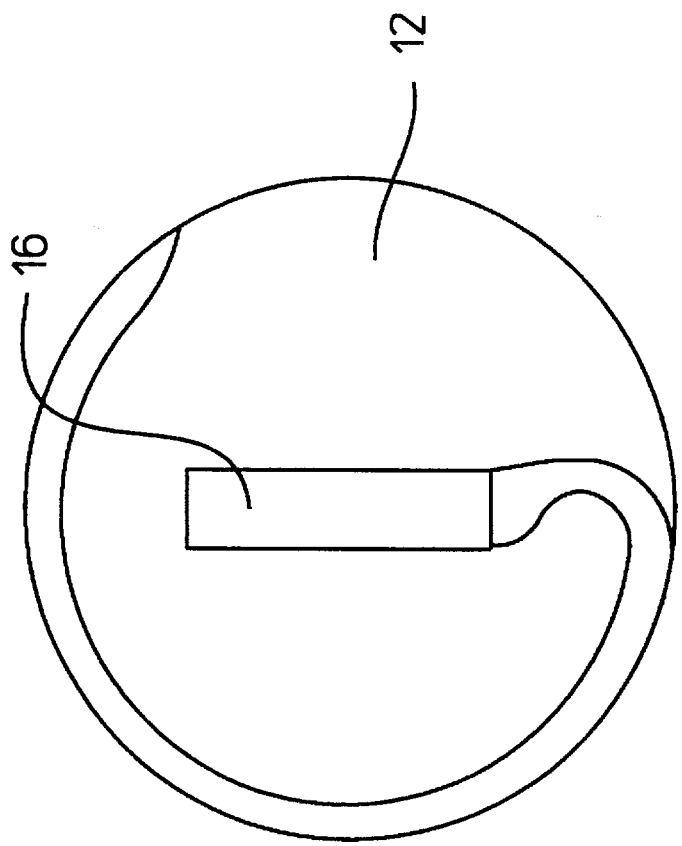
FIG. 2 illustrates the shape of the central cavity.

FIGS. 1A–C illustrate a preferred embodiment for a miniature rotatable sensor 2. FIG. 1A shows a side view of the sensor while FIG. 1B shows a cross-sectional view of the sensor. FIG. 1C illustrates a bottom view of the sensor. An acoustic face 10 is positioned over a layer of attenuating material 12. A flexible circuit 14 contacts the acoustic face 10 and extends beyond the attenuating material 12 to create an inner portion of the attenuating material 12A. The inner portion of the attenuating material 12A has a radial slot 16. The outer edges of the flexible circuit 14 are folded into the radial slot 16 such that the flexible circuit 14 exits tangential to the diameter of the sensor 2.

FIG. 2 illustrates the shape of the radial slot 16. It extends deep into the attenuating material 12. A bent portion of the radial slot 16 positions the exiting flexible circuit 14 circuit tangential to the diameter of the sensor 2.

Figure 3:
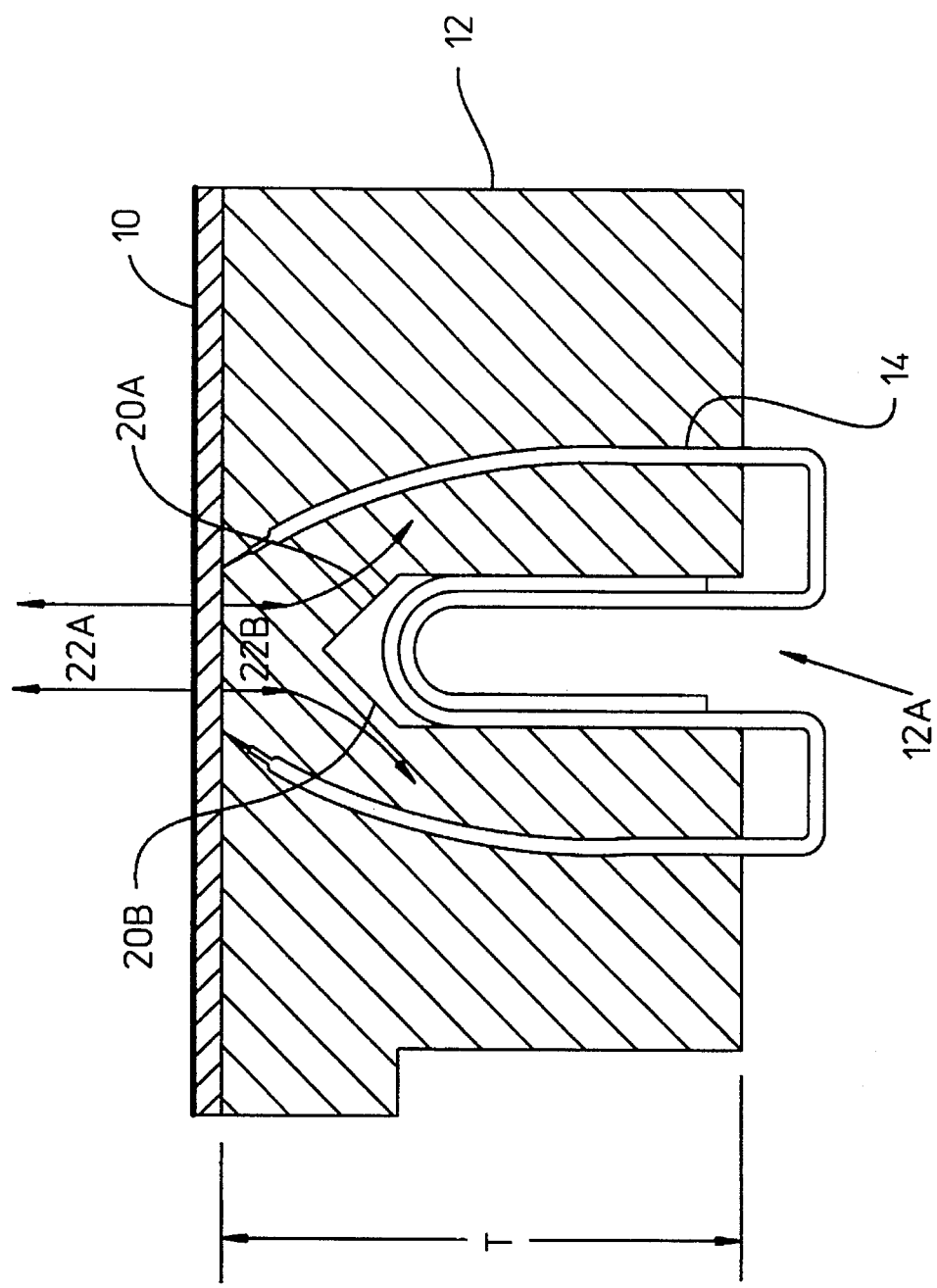
FIG. 3 illustrates the shape of the bottom of the central cavity.

FIG. 3 illustrates the shape of the bottom of the radial slot. The bottom of the radial slot 16 has two angled walls 20A, 20B that divert the reflected acoustic energy away from the acoustic face 10. The acoustic face 10 generates acoustic waves that travel in two directions: into the human body 22A and into the attenuating material 22B. The waves travelling into the attenuating material 22B are undesirable. The thickness of the attenuating material T is selected such that the wave reflected from the bottom of the attenuating material will affect the performance of the sensor. If the radial slot 16 had a flat bottom, the distance of round trip travel of the wave would be smaller than T and could create a problem. As a result, the walls of the radial slot 20A, 20B are angled to deflect the wave to increase the distance of round trip travel.

Figure 4:
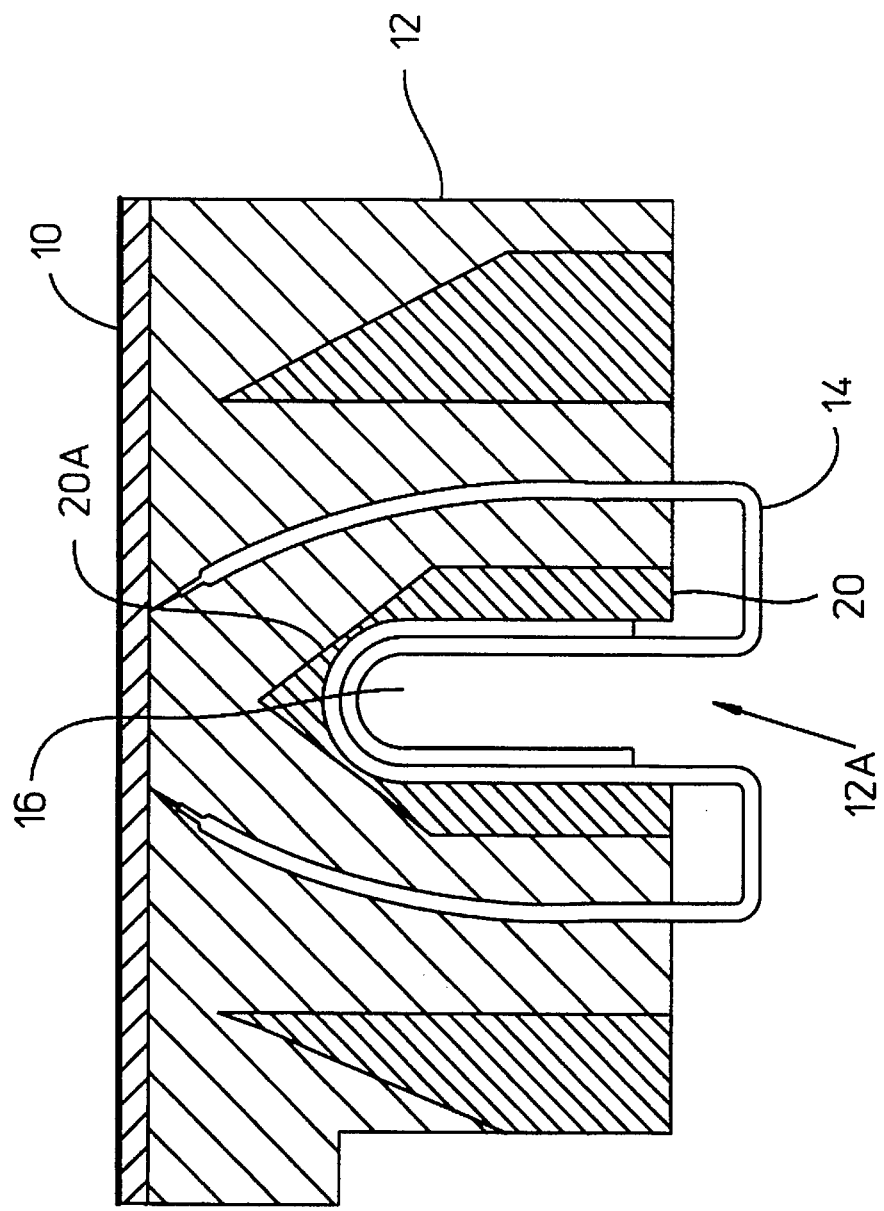
FIG. 4 illustrates another preferred embodiment for a miniature rotatable sensor (with the heat sink).

FIG. 4 illustrates another embodiment for the miniature rotatable sensor 2 with the heat sink. In this embodiment, the inner portion 12a includes a heat sink 20 for better heat dissipation. The top part of the heat sink 20 has angled walls 20a to divert the reflected acoustic energy away from the acoustic face 10. The back side of the heat sink 20 has a radial slot 16 extending to the circumference of the sensor 2. The outer edges of the flexible circuit 14 is folded into the radial slot 16.

Figure 5:
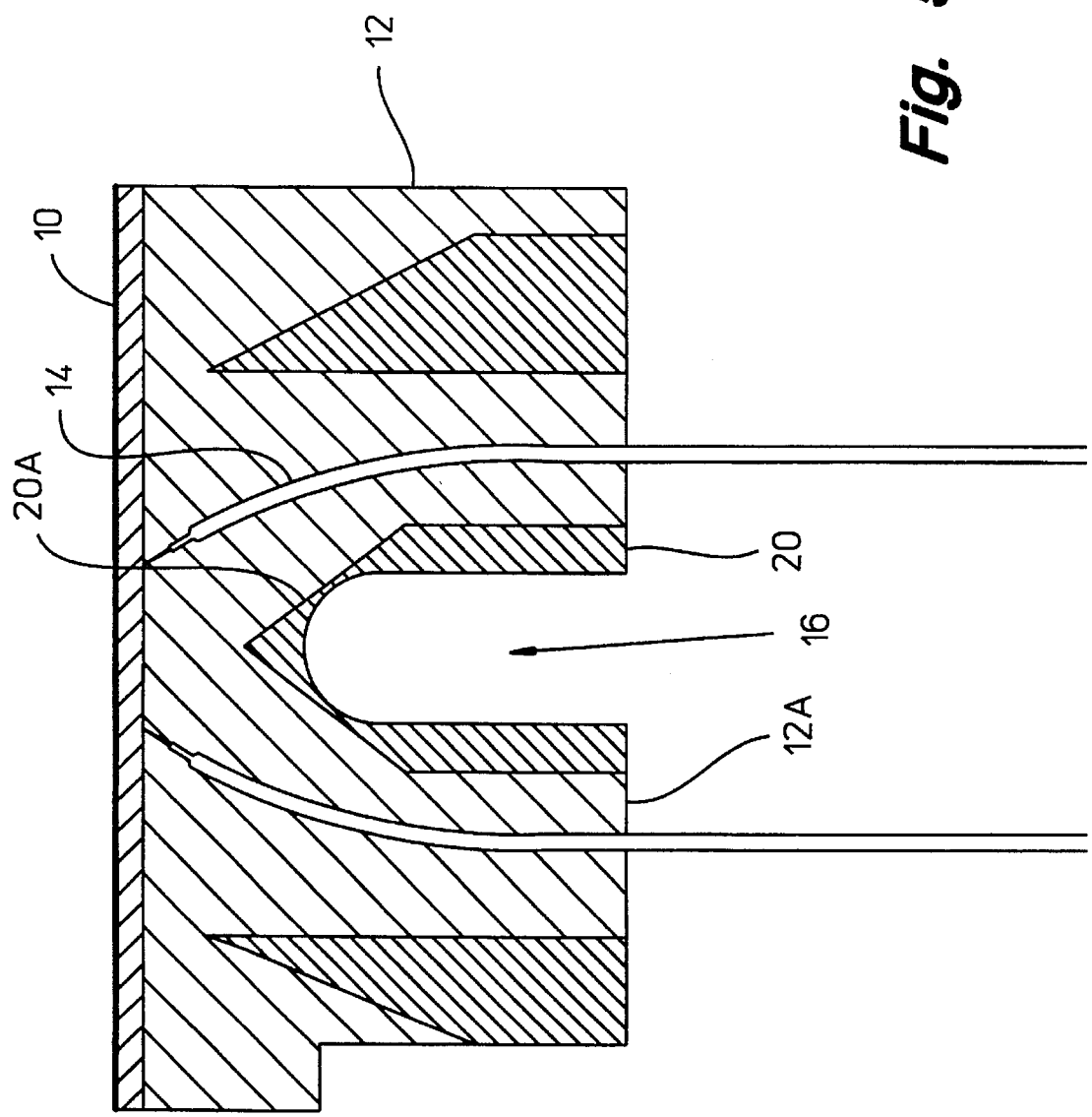
FIG. 5 illustrates the preferred embodiment before the flexible circuit is folded into the central cavity.

FIG. 5 illustrates the embodiment shown in FIG. 4 prior to folding the outer portions of the flexible circuit 14 into the radial slot 16.

We claim:

1. A miniature rotatable sensor for transesophogeal imaging comprising:
   a sensor having an acoustic face;
   a layer of attenuating material, having a diameter, contacting the acoustic face;
   a flexible circuit contacting the acoustic face and the layer of attenuating material, wherein the flexible circuit has edges that extend beyond the layer of attenuating material; and
   the layer of attenuating material including a radial slot positioned along the diameter, the edges of the flexible circuit being positioned within the radial slot.

2. A miniature rotatable sensor, as defined in claim 1, wherein the bottom of the radial slot has angled walls that divert acoustic energy away from the acoustic face.

3. A miniature rotatable sensor, as defined in claim 1, the layer of attenuating material further comprising a heat sink, being of thermally conductive material, that forms the radial slot.

4. A miniature rotatable sensor, as defined in claim 3, wherein the heat sink has angled walls that divert the reflected acoustic energy away from the acoustic face.

* * * * *